United States Patent [19]
Mitchell et al.

[11] Patent Number: 5,223,250
[45] Date of Patent: Jun. 29, 1993

[54] VISIBLY TRANSPARENT UV SUNBLOCK COSMETIC COMPOSITIONS

[75] Inventors: Kim Mitchell, Granada Hills, Calif.; Mark Mitchnick, Wainscott, N.Y.

[73] Assignee: Sun Smart, Inc., Wainscott, N.Y.

[21] Appl. No.: 651,696

[22] Filed: Feb. 5, 1991

[51] Int. Cl.$^5$ .................. A61K 7/42; A61K 7/44; A61K 9/10; A61K 9/14
[52] U.S. Cl. ........................ 424/59; 424/60; 424/63; 424/64; 424/401; 514/844; 514/847; 514/938
[58] Field of Search ............ 424/59, 60, 401

[56] References Cited

U.S. PATENT DOCUMENTS

| | | | |
|---|---|---|---|
| 2,175,213 | 10/1939 | Parsons | 167/90 |
| 3,226,297 | 12/1965 | Thuresson et al. | 424/59 |
| 3,425,844 | 2/1969 | Flinn et al. | 424/59 |
| 3,441,579 | 4/1969 | Isoura | 424/59 |
| 3,574,822 | 4/1971 | Shepherd et al. | 424/59 |
| 4,172,122 | 10/1979 | Rubik et al. | 424/59 |
| 4,349,536 | 9/1982 | Hausler | 424/59 |
| 4,486,405 | 12/1984 | Klein | 424/59 |
| 4,822,600 | 4/1989 | Wortzman | 424/59 |
| 4,828,825 | 5/1989 | Weber et al. | 424/59 |
| 4,861,651 | 8/1989 | Goldenhersh | 428/255 |
| 4,882,143 | 11/1989 | Kadokura et al. | 424/59 |
| 4,917,882 | 4/1990 | Strobridge | 424/59 |
| 4,925,653 | 5/1990 | Grollier et al. | 424/47 |

OTHER PUBLICATIONS

The Merck Index, 1976, 9812.
Cosmetics Science and Technology, 1957, pp. 197, 203, 204, 1095, 1101 and 1102.
Hurwitz, The Sun and Sunscreen Protection: Recommendations for Children, *Dermatol. Surg. Oncol.*, 14:6, p. 657 (Jun. 1988).
Pathak, Sunscreens and Their Use in the Preventive Treatment of Sunlight-Induced Skin Damage, *Dermat. Surg. Oncol.*, 13:7, p. 739 (Jul. 1987).
Pathak, Sunscreens: Topical and Systemic Approaches For Protection of Human Skin Against Harmful Effects of Solar Radiation, *J. Amer. Acad. Dermatol.*, 7, p. 285 (1982).
Taylor et al., Photoaging/Photodamage and Photoprotection, *J. Amer. Acad. Dermatol.*, 22:1, p. 1 (1990).
Optical Plastics: Properties and Tolerances, The Photonics Design and Applications Handbook, p. H-209 (1985).

(List continued on next page.)

*Primary Examiner*—Dale R. Ore
*Attorney, Agent, or Firm*—Pennie & Edmonds

[57] ABSTRACT

Cosmetically acceptable physical sunscreens which remain visibly transparent upon the skin while remaining capable of absorbing substantial UV radiation. A first embodiment is directed to the use of a dispersion of micronized particles of zinc oxide having a very low trace metal content. A second embodiment utilizes substantially larger crystals of substantially pure zinc oxide, measuring between about 1-100 microns in diameter, formed by a process, such as chemical vapor deposition, which produces symmetrical, substantially optically perfect crystals with a relatively smooth outer surface and which are substantially free of internal fractures and imperfections. Visibly transparent glass particles having a diameter of between about 0.01–100$\mu$ may also be utilized as the UV-absorbing agent. A further embodiment utilizes visibly transparent plastic spheres measuring between about 0.01-100 microns in diameter and having incorporated therein at least one UV-absorbing additive for adjusting the bandgap energy of such spheres to the border between the visible and the ultraviolet wavelength ranges. The particulate materials described above are preferably dispersed into an emulsion to facilitate their application onto the surface of the user's skin. The invention further comprises cosmetic formulations having incorporated therein the particulate sunblock agents described above.

14 Claims, No Drawings

OTHER PUBLICATIONS

Abramoff, Ultravoilet Stabilizers, Modern Plastics Encyclopedia (1976-1977) pp. 222, 224, 227 708 and 709.

Plexiglas ® Design & Fabrication Data, PL-1p, Rohm & Haas Company (1983).

Plexiglas ® Design & Fabrication Data, PL-612d, Rohm & Haas Company (1979).

Dromgoogle, Sunscreening Agent Intolerance: Contact and Photocontact Sensitization and Contact Urticaria, *J. Amer. Acad. Dermatol.*, 22, p. 1068 (1990).

Eberspacher, Properties of ZnO Films Deposited Onto INP By Spray Pyrolysis, Thin Solid Films, 136, p. 1 (1986).

Brown, *Zinc-Oxide: Properties and Applications*, pub. by International Lead and Zinc Research Organization, Inc. pp. 11-12 (1976).

Alnsworth, Move to Natural Cosmetics Challenges Ingredient Suppliers, Chemical & Engineering News (Nov. 26, 1990).

VISIBLY TRANSPARENT UV SUNBLOCK COSMETIC COMPOSITIONS

TECHNICAL FIELD

The present invention relates generally to particulate materials adapted for use as sunblocking agents and more particularly to the use of these materials in transparent, cosmetically acceptable UV sunscreen products as well as in improved cosmetic formulations having an increased ability to protect the user from UV radiation.

BACKGROUND OF THE INVENTION

One portion of the solar spectrum comprises wavelengths of electromagnetic energy which range between about 290 and 3,000 nanometers (nm). This range may be divided into different regions, namely: (1) the ultraviolet region (290–400 nm), (2) the visible region (400–760 nm) and (3) the near-infrared region (>760 nm). The ultraviolet region has, moreover, been arbitrarily divided into three bands, referred to as the UVA, UVB and UVC bands.

The UVB band extends from 290 to 320 nm. It is the principal cause of the sunburn reaction and it is also the most effective in stimulating the tanning reaction in the skin. UVC radiation (200–290 nm) from the sun does not reach the surface of the earth, although one can encounter radiation in this range from artificial sources such as germicidal lamps and high and low pressure mercury arc lamps. For purposes of the present invention however, protection against UVC radiation is generally not a major concern, i.e., in contrast to the dangers posed by UVA and UVB radiation. The UVA band, which extends from 320–400 nm, can also cause the tanning reaction. UVA radiation can also cause sunburns, but its capacity to do so is less than that of UVB radiation.

The amount of UVA radiation exposure, however, is increasing. This is due to the fact that most sunscreens effectively block only UVB radiation. As stated above, UVB radiation is more capable than UVA radiation of causing the tanning and burning reactions. Therefore, if one is using a sunscreen that blocks UVB radiation he/she will tend to stay in the sun for an extended period of time because the immediate effects of the sun tan/burn are not evident. The problem is that UVA is still penetrating the skin and although it is not causing any immediately obvious effects, it is causing long term damage. In recent years, it has been well documented that UVA radiation, like UVB radiation, is harmful to the skin. In fact, current data reveal that solar radiation containing these wavelengths is the chief cause of skin cancer, which presently accounts for 30–40% of all new cancers each year. In the United States alone, 500,000 new cases of skin cancer will be reported this year and the number is expected to keep rising in the future. UVA radiation has been shown to promote skin cancer by inhibiting enzymes that repair cells damaged by UVB radiation. UVA radiation also penetrates more deeply into the skin than UVB radiation and causes changes in blood vessels and premature aging of the skin, thus adding to the damage produced by UVB rays (see, e.g., Hurwitz, Sidney, "The Sun and Sunscreen Protection: Recommendations for Children", *Dermatol. Surg. Oncol;* 14:6 (June 1988) p. 657). The goal of any sunscreen should thus be to protect the user from both UVA and UVB radiation with a minimum of side effects. This end has not been adequately achieved with the use of presently available sunscreen products.

Sunscreen products can be grouped into two broad categories, i.e., (1) topical sunscreens and (2) oral sunscreens. The present invention focuses upon the topical sunscreens, which can be further differentiated into two subcategories, namely (1) chemical sunscreens and (2) physical sunscreens.

Chemical sunscreens contain from about 3 to about 26% of one or more UV-absorbing chemicals. When applied to the surface of the skin as a thin film, i.e., about 10–15 $\mu$m in thickness, these chemicals act as a filter to diminish the penetration of UV radiation to the cells of the epidermis. These sunscreens are typically applied in a cream, oil, lotion, alcohol or gel vehicle and they are usually colorless because they do not contain any visible light-absorbing chemicals. The most widely used chemical sunscreens contain, for example, para-aminobenzoic acid (PABA), PABA esters (glyceryl PABA, amyldimethyl PABA and octyldimethyl PABA), benzophenones (oxybenzone and sulisobenzone), cinnamates (octylmethoxy cinnamate and cinoxate), salicylates (homomethyl salicylate) and anthranilates. To date, more than twenty-one such chemicals have been approved by the United States Food and Drug Administration as "safe and effective" agents in protecting skin against sunburn (see, e.g., Pathak, Madhu, "Sunscreens: Topical and Systemic Approaches for Protection of Human Skin Against Harmful Effects of Solar Radiation", Continuing Medical Education Series, *J. Am. Acad. Dermat.*, 7:3 (September 1982) p. 285, 291).

Questions have recently been raised, however, by the medical profession as to whether the chemical components of these sunscreens are indeed inert and further, whether repeated use of such sunscreens can result in significant transdermal absorption of these chemicals. Because chemical sunscreens are applied topically in relatively high concentrations (i.e., up to 26%), contact and photocontact sensitization can occur, as well as hypersensitivity, i.e., photoallergic reactions (see Drumgoogle et al., "Sunscreening Agent Intolerance: Contact and Photocontact Sensitization and Contact Urticania", *J. Am. Acad. Dermatol.*, 1990:22, p. 1068).

Physical sunscreens, on the other hand, comprise particles of a relatively physiologically inert sunblock, i.e., UV-absorbing, compound typically suspended in a cream or lotion. Materials frequently utilized for this purpose include kaolin, talc and two metal oxides, i.e., titanium dioxide and zinc oxide. The latter two compounds are not associated with the inflammatory reactions noted above.

The physical sunscreen products are, however, typically messy and occlusive. Moreover, they additionally form a visible, colored (e.g., white) layer on the surface of the skin which is cosmetically unacceptable to many who are in need of sunscreen protection. This causes many such individuals to forego the use of these products. The color of these compositions is attributable to the optical properties of the particles from which these materials are formed. These properties are at least partially dependent upon the size of these particles, which typically have a fairly "standard" range of diameters, measured in tenths of a micron (i.e., about 0.1–0.9$\mu$).

In addition, presently available physical sunscreens are not easily washed off of the user's body. Instead, they typically melt off with the heat of the sun, thus incidentally staining or otherwise discoloring the user's clothing. Moreover, because they are applied as relatively thick films (20–50 μm), use of these products may also promote undesirable skin conditions, including miliaria, a skin disease caused by an inflammation of the sweat glands, and folliculitis, an inflammation of the hair follicle. As such, these physical sunscreen products are deemed cosmetically unacceptable by a large class of image conscious persons, which primarily includes young people. Unfortunately, this same group is the exact population that needs solar protection the most. It has been stated that proper use of sunscreens prior to the age of 18 would prevent 80% of skin cancers (see, e.g., Taylor et al., "Photoaging/Photodamage and Photoprotection", 22 *J. Am. Acad. Dermatol.*, 9 (1990)).

In one variant of the "typical" prior art physical sunblocks described above, certain commercial sunscreen products containing titanium dioxide are made with what is known as "micronized" or "large surface area" particles of the metal oxide. These particles have a diameter an order of magnitude smaller (i.e., measuring about 0.01μ) than the "standard" sized particles (measuring about 0.1–0.9μ) described above. One drawback to the use of this material, however, is that titanium dioxide absorbs neither as much UV-radiation nor transmits as much visible radiation as, for example, zinc oxide, which is utilized by applicants in the present invention (see, e.g., Brown, Harvey E., *Zinc Oxide: Properties and Applications*, pp. 11–12, FIG. 2–4 (1976)). Thus, although the use of micronized titanium dioxide particles does render the resultant product smoother and less occlusive, it does not obviate the main drawback faced with the use of this material, i.e., its comparatively lower effectiveness (in contrast to ZnO) as a sunblock agent. Titanium dioxide-based products are also more opaque than those formed with the zinc oxide of the present invention, which is due to the fact that the crystalline structure of the titanium dioxide material renders it only partially transparent to visible wavelengths of light and thus not generally as acceptable for cosmetic use.

Although it has been known to form micronized particles of zinc oxide for very specialized uses in the rubber industry, these particles contain substantial quantities (i.e., greater than about 200 ppm) of trace metals such as lead, mercury, arsenic and cadmium. The potential dangers to human health caused by exposure to these materials is well-documented. Thus, such zinc oxide particles containing these levels of trace metals are not acceptable for topical application to human skin.

Greater public awareness of the harmful effects of exposure to excessive solar radiation has therefore resulted in an increased use of sunscreen products by the public, coupled with a call for improved sunscreen materials free of the drawbacks described above by those whose livelihood and/or leisure activities cause them to be exposed to any substantial amounts of solar radiation.

SUMMARY OF THE INVENTION

It is thus an object of the present invention to provide new, improved cosmetically acceptable physical sunblock materials capable of absorbing a greater degree of ultraviolet radiation so as to prevent the user's skin from being damaged by exposure to these solar rays.

It is a further object of the present invention to provide sunscreen products utilizing sunblocks of the type described above which are capable of effectively absorbing UVA and UVB radiation while retaining a substantially visibly clear appearance upon the surface of the skin.

It is a still further object of the present invention to provide visibly transparent physical sunblocks which do not cause adverse chemical reactions upon the skin of the user.

It is another object of the present invention to provide a variety of improved cosmetic formulations containing the particulate sunblock materials described herein which offer an enhanced degree of solar protection to the user.

In a first embodiment, therefore, the invention is directed to a sunscreen formulation comprising micronized particles of a zinc oxide sunblock suspended in a dermatologically suitable liquid carrier, preferably in the form of an emulsion. These micronized particles, as now produced by applicants, are formed using known techniques, such that the resultant particles have acceptable, i.e., reduced, levels of trace metals such as cadmium, arsenic, mercury, lead, etc., which levels are set forth in Table I below. These levels are substantially lower than those found in the particles described above for use in the rubber industry where toxicity is not a concern. Applicants' particles, having the requisite levels of these trace metals for use in the present invention, are therefore referred to in the present specification as substantially "pure". This substantially "pure" material is thus suitable for application to human skin since the trace metal content is maintained at or below the levels set forth in Table I below, that is, below levels which are likely to cause dangerous effects in humans.

Zinc oxide particles of the size and morphology described below, with such reduced levels of trace metal contamination, have not been previously known in the art, as far as applicants are aware. There has, in fact, been no call for this substantially pure form of zinc oxide since, as described herein, the use of this visually transparent UV-sunblock material was not previously contemplated by those working in the sunscreen or the cosmetic fields.

In a preferred embodiment, applicants' substantially pure zinc oxide particles are formed having a substantially spherical shape. This shape is preferred because it provides a smooth "feel" on the skin of the user. A variety of other crystalline shapes, such as needles, rhomboids, etc. have also been found to provide acceptable UV protection, however, and may be utilized in the formulations of the invention as well, although as noted above, spherical particles are the most preferred. On the basis of the optical properties of the substantially pure micronized zinc oxide particles developed by applicants, sunscreen products formed with this material remain visibly transparent on the skin while absorbing a greater portion of the UVA and UVB radiation than was previously possible with the use of prior art sunblock compositions, without resulting in any adverse effects caused due to transdermal absorption. This result is not possible with the only other commonly used metal oxide, i.e., titanium dioxide, due to the different, i.e., less effective, optical properties exhibited by titanium dioxide.

A second embodiment of the present invention is directed to the formation of physical sunscreen products comprising a particulate zinc oxide sunblock, preferably spherical in shape, having a diameter of an order of magnitude greater than the "standard size" (i.e., 0.1–0.9μ) particles used in prior art sunscreen compositions described above. The particles used in the subject embodiment are thus also substantially larger than the micronized particles described for use with the previous embodiment, i.e., they measure at least about 1 micron, and preferably between about 1-100 microns in diameter. At diameters above about 100µ, the optical performance of this material appears to deteriorate somewhat.

What is required, however, is that these particles be prepared by a process, such as gas phase chemical vapor deposition (CVD), spray pyrolysis or sol-gel particle formation, which results in the formation of symmetrical, substantially "optically perfect" crystals which are essentially free of internal fractures and/or other physical imperfections, and which have a relatively smooth outer surface. Such crystals, as a result of their morphology, have the required optical properties for use with the sunscreen formulations of the present invention, i.e., they absorb a substantial portion of the ultraviolet radiation to which, they are exposed, which, as noted above, is greater than that which is absorbed with the use of prior art sunblock products, while remaining transparent in the range of visible wavelengths.

In addition, the relatively large crystals of the subject embodiment are also substantially pure as described above and thus contain only insignificant amounts of the trace metals listed in Table I below. The "purity" of these particles renders sunscreen formulations containing this sunblock material suitable for topical application to human skin without danger due to transdermal absorption of trace metals. The substantially pure zinc oxide particles are incorporated into a liquid carrier, such as the emulsion described above, to form a visibly transparent sunscreen formulation capable of absorbing a substantial portion, if not all, of the ultraviolet radiation directed upon the skin of the user to which this material is applied.

Alternately, in a further embodiment, particles of a visibly transparent UV-absorbing glass may be substituted within the emulsion for the zinc oxide particles described above. The glass particles used in the subject embodiment have an average diameter ranging between about 0.01-100 microns. They must also possess a relatively smooth outer surface and be substantially free of internal fractures or other physical imperfections. One well-known optical glass composition which has been shown to provide the desired results is referred to as Corning BK-7 (i.e., borosilicate crown-7) glass. The formulation of this material is well known and thus need not be described herein.

A still further embodiment of the present invention comprises a physical sunscreen formed with a plurality of small, visibly clear plastic spheres measuring between about 0.01-100 microns in diameter. To obtain the proper optical performance, one or more UV-absorbing compounds, which may be chosen from a variety of materials well known in the art, are incorporated into the plastic used to form these spheres. The UV-absorbing compound, once incorporated into the plastic spheres, can no longer react with or be absorbed by the skin. These UV-absorbent spheres are then dispersed in a liquid vehicle, such as the emulsion discussed above, to form a visibly transparent sunscreen lotion which may be topically applied to prevent ultraviolet radiation from reaching the skin of the user.

The particulate materials described above for use in the sunscreen formulations of the present invention may also be incorporated by known blending methods into a variety of cosmetic products such as lipstick, eyeshadow, foundations, moisturizer, rouge and the like to form cosmetics having an increased ability to prevent damage to underlying skin by the action of solar UV radiation.

DETAILED DESCRIPTION OF THE PREFERRED EMBODIMENTS

In selecting particulate materials for use in forming applicants' 1) sunscreen products, and 2) cosmetic formulations containing the sunblocking agents of the invention, three optical properties, i.e., the absorption, reflection and refraction of these materials, must be considered.

With regard to the first of these properties, i.e., optical absorption, it will suffice to note that, for purposes of the present invention, this parameter is defined by a characteristic optical energy known as the "bandgap" energy. Semiconductor materials such as the metal oxides, the visibly transparent glasses (e.g., BK-7) and UV-absorbing plastics described herein are transparent to wavelengths above this bandgap value while they absorb energy having a wavelength lower than the bandgap energy. Thus it is preferred to use materials whose bandgap energies are such that they remain visibly transparent while absorbing wavelengths of light below about 400 nm, i.e., in the ultraviolet range.

Optical reflection and refraction are the remaining properties which must be taken into account in predicting the performance of the particulate materials chosen for use in the present invention. With regard to these properties, it is important to note, first, that the ability of a particle to reflect light is affected by the morphology of the surface of the material of which the particle is formed, by the angle of light incident to the surface of the material and by the difference in the index of refraction of the material compared to that of the surrounding media. That is, the closer the refractive index of the particulate material is to that of the medium in which it is suspended, the less visible contrast there will be. Formulation bases for use on human skin typically have a refractive index of no greater than about 1.6 while the refractive index of titanium dioxide is about 2.5 and that of zinc oxide is about 1.9. This difference makes it possible for zinc oxide to more readily blend with a suitable base while not significantly contributing to that mixture's visible optical properties.

Secondly, particles, i.e., crystals, formed with rough surfaces or having internal fractures or other physical imperfections will scatter incident light more than smooth particles and/or those lacking such fractures and imperfections. It is thus preferred to use particles having a substantially smooth outer surface which are relatively free of internal fractures and imperfections in the present invention. This enables sunscreen products formed with these sunblock materials to absorb a substantial portion of the UV wavelengths to which the user is exposed while remaining substantially transparent on the surface of the skin.

The substantially pure zinc oxide of applicants' invention, i.e., having a minimal trace metal content as set forth in Table I below, is preferred for use herein in order to take advantage of the abrupt transition which zinc oxide undergoes from reflector to absorber at a bandgap energy corresponding to a wavelength of about 385 nm, i.e., substantially at the border between the UV and the visible regions. This bandgap energy value is in marked contrast to that of titanium dioxide, which does not show the same sharp change in transmission upon entering the ultraviolet region (see, e.g., Brown, Harvey E., *Zinc Oxide: Properties and Applications*, pp. 11-12 (1976)).

A further advantage to the use of zinc oxide over titanium dioxide in the sunblock formulations of the present invention is that zinc oxide is substantially less expensive than titanium dioxide, thus providing a significant cost savings with the use of this material in applicants' invention. Still further, as noted above, applicants' substantially pure micronized zinc oxide particles contain a substantially lower amount of trace metals than is typically found in the specialty purpose micronized particles of this material. The use of such prior art micronized zinc oxide is, as discussed above, not possible because of the toxicity of this material due to the relatively high concentrations of trace metals contained therein.

Turning now to the first embodiment of the present invention, applicants have discovered that their substantially pure micronized particles of zinc oxide (described below), when dispersed in a dermatologically suitable liquid carrier in the form of a colorless emulsion, form a visibly transparent sunscreen when applied to human skin. This formulation is capable of absorbing a substantial quantity, if not all, of the UV radiation to which the user is exposed. As noted above, these zinc oxide particles are preferably spherical in shape to provide a "smooth" feel to the product and to facilitate its application onto the skin, but non-spherical particles, such as needles, squares, rhomboids, etc., may also serve the required purpose, although they are not as preferred.

Although, as noted above, micronized particles of zinc oxide are known in the art for specialty applications in the rubber industry, such particles contain elevated levels, i.e. greater than 200 ppm, of toxic trace metal contaminants. These trace metals include lead, cadmium, mercury and arsenic, all of which are known to be hazardous to human health. In contrast, the "substantially pure" zinc oxide particles developed by applicants for use in the present invention, whether in the form of micronized particles or as larger, "optically perfect" particles as described above, contain no more than the following ranges of the trace metals listed below:

TABLE I

| | |
|---|---|
| lead | <20 ppm |
| arsenic | <3 ppm |
| cadmium | <15 ppm |
| mercury | <1 ppm |

There is no teaching or suggestion that applicants are aware of after an extensive review of the literature in this field to utilize zinc oxide particles of the type described herein in applications such as those contemplated by applicants, namely as a component of: 1) transparent sunscreen formulations or 2) cosmetic compositions capable of providing an enhanced degree of protection from solar rays. Thus the use of applicants' substantially pure particles in the manner indicated provides totally unexpected results with regard to the ability of this material to protect the user against the effects of solar radiation containing UV wavelengths.

Suitable carriers for forming the emulsion described above include SD alcohol, lanolin, glyceryl stearate, cocoa butter, sorbitan sesquioleate, propylene glycol, mineral oil, isopropyl myristate, petrolatum and acrylic polymers. Mixtures of two or more of these materials may also be used. These materials are known in the art as being "dermatologically suitable", i.e., they do not cause or promote adverse reactions upon the skin of the user.

The amount of the carrier need only be sufficient to provide a uniform dispersion of the particles when they are applied to the skin to ensure adequate coverage of the skin with the UV-absorbing material. The particulate material preferably comprises no more than about 20% by weight of the total emulsion and preferably between about 1-10% by weight thereof. The only real limit on the lower end of this concentration range is that a sufficient quantity of the particulate must be included to permit the formulation to absorb the desired amount of UV light. Concentrations of less than about 1% by weight of the total composition may even be useful in some instances.

In comparing the optical performance of particles of micronized, i.e., "high surface area", zinc oxide, having a diameter measuring about $0.01\mu$, to that obtained with the use of "standard" sized particles of this material (having a diameter of between about $0.1-0.9\mu$) typically incorporated in presently available zinc oxide sunscreen compositions, applicants have found that, since the size of the micronized particles is well below that necessary for most efficient light scattering, a film of such micronized particles, dispersed in a suitable liquid vehicle such as an emulsion formed of a dermatologically suitable carrier as described above, will transmit a sufficiently large percentage of visible light to appear visibly transparent, while remaining essentially opaque to UV radiation.

A second embodiment of the applicants' sunblock formulations comprises substantially pure particles of zinc oxide, preferably spherical in shape, having a diameter substantially greater by at least an order of magnitude than the "standard" sized zinc oxide particles used with prior art sunscreen compositions described above and about two orders of magnitude greater than the micronized zinc oxide particles. Thus, the zinc oxide particles preferred for use in the subject embodiment of the invention measure at least about 1 micron in diameter, and preferably between about 5-20 microns. The upper end of this range is not critical, however and thus the subject particles may range up to 50 or even 100 microns in diameter. Furthermore, the particles need not be spherical, although that shape is preferred since it facilitates application of the sunblock composition onto the skin when the zinc oxide particles are dispersed in a liquid carrier such as the emulsion discussed above. The concentration of these particles within the emulsion is essentially the same as that used for the embodiment utilizing micronized zinc oxide, i.e., between about 1-20% by weight and preferably between about 1-10% by weight.

As noted above, the bandgap energy value of zinc oxide is such that it changes from transparent to opaque at approximately the border between visible and UV light. However, as previously discussed, if the zinc oxide particles have rough surfaces or if they have internal fractures or other physical imperfections, these features will contribute to the scattering of incident light and a sunscreen product formed of such a material will thus not be visibly transparent.

In order to overcome these difficulties, the substantially pure zinc oxide particles of the subject embodiment are preferably formed with the use of a chemical vapor deposition ("CVD") technique, which results in the formation of symmetrical particles of zinc oxide having a diameter within the range noted above, which appear visibly clear upon the surface of the skin while remaining capable of absorbing a substantial portion of the UV radiation to which they are exposed. These particles are thus considered by applicants to be substantially "optically perfect" for the purposes of their invention.

In the CVD process used with the present invention, zinc source compositions are introduced as vapors into a heated reaction volume, i.e., chamber, where they react with oxygen, typically supplied as a gas, to form the zinc oxide particles described above, i.e., ranging in size from about 1 to about 100 microns. The driving force for this reaction can be the exothermic formation energy of the zinc oxide product itself or this energy may instead be supplied by external sources such as thermal or radio frequency (RF) plasma energy. The entire process may be automated and computer controlled in a manner known in the art.

More specifically, the CVD process utilized by applicants may utilize, as a zinc source, compositions such as zinc acetate, zinc chloride, zinc oxalate or organometallic zinc compounds such as dimethyl zinc ("DMZ") and dimethyl zinc ("DEZ"). Applicants have determined that zinc oxide formed with the use of CVD from an organometallic zinc source will achieve particles having high growth rates at relatively low growth temperatures, i.e., below 500° C. and are thus preferred. The zinc sources used are thus preferably DMZ and DEZ, whereas the oxidizing gas may be selected from among gaseous water, oxygen and alcohol.

Since both DEZ and DMZ are liquids, they are contained, prior to use, in a conventional bubbler device, typically maintained at about 20° C., whereupon they are subsequently transferred to the reactor via a carrier gas such as nitrogen or argon which is bubbled through the liquid. Water vapor is introduced to the reactor in a similar manner. The zinc and oxidizer source chemicals are injected into the hot reaction chamber through separate nozzles where they mix and react to form the zinc oxide particles. The ratio of oxidizing gas to the organometallic zinc should be greater than about 7:1, preferably about 10:1, in order to completely oxidize the zinc. The reaction temperature may range from about 180° to about 500° C., with the preferred range being from about 300° to 400° C. The reaction pressure can range from 1 torr to about 760 torr. For purposes of simplifying the apparatus, however, atmospheric pressure is preferred.

The desired zinc oxide particle size is achieved by (1) manipulating the amount of reactants used by, for example, a mass flow-controller, and (2) the residence time of these materials in the reactor. The relationship between these parameters is such that, for example, increasing the amount of time the reactants spend in the reaction chamber will result in a proportional size increase in the zinc oxide particles thus formed. The resultant substantially pure zinc oxide particles, having a diameter ranging in size from about 1-100 microns, are formed with a substantially smooth outer surface and, in addition, are substantially free of internal fractures and/or other physical imperfections. Moreover, if desired, an antireflection coating of, for example, silicon oxide may be applied to the surface of these particles to reduce the optical reflection from the material/media interfaces which thus renders them even more transparent to visible light.

Alternately, in place of the CVD process described above, acceptable zinc oxide particles may be formed with the use of other conventional processes such as spray pyrolysis (see, e.g., Eberspacher et al., "Pyrolysis of ZnO Film Deposited Onto InP By Spray Pyrolysis," *Thin Solid Films*, 136 (1986, pp. 1-10) or sol-gel particle formation, both of which are well known to those skilled in the art.

Moreover, it is important to note that although zinc oxide and other metal oxide compositions have previously been commercially utilized in the form of relatively thick visibly transparent layers used, for example, in forming heat mirrors in architectural applications and as transparent electrical conductors for solar electric applications, the present invention is directed to the formation and use of separate, dispersed substantially pure zinc oxide particles in a liquid carrier to serve as a visibly transparent, UV-absorbent sunblock. Moreover, the inclusion of such relatively "optically perfect" visibly transparent, UV-absorbent particles of zinc oxide in sunscreen compositions of the type described herein has not, to applicants' knowledge, been contemplated anywhere in the prior art.

In a further embodiment of the invention, particles of a visibly transparent glass having a bandgap energy at about 400 nm, thus permitting it to absorb UV light while remaining virtually transparent to visible light, may be dispersed in the carrier in place of the 1-100μ zinc oxide particles described above. The diameter of the glass particles preferred for use in the invention may range between about 0.01-100 microns. In addition, these glass particles must have a substantially smooth outer surface and be substantially free of internal fractures and other imperfections. Any such optical glass meeting the requirements set forth above may be utilized, although borosilicate glasses such as the visibly transparent Corning BK-7 material described above are preferred for use with the present invention. The antireflective coatings described above may also be used to coat the optically active glass particles of the type described herein.

Another embodiment of the invention comprises a sunscreen lotion including a plurality of commercially available plastic particles preferably, although not necessarily, spherical in shape with a diameter ranging between about 0.01-100μ, formed, in part, of a visibly transparent plastic. Such plastics are well-known in the art and may include, for example, acrylics such as polymethyl methacrylate ("PMMA"); styrene polymers; copolymers of styrene and acrylic; styrene acrylonitrile ("SAN"); polycarbonate; methylpentene; terpolymers of acrylonitrile, butadiene and styrene ("ABS") and allyl diglycol carbonate ("ADC"). The invention should not, however, be limited to the use of these plastics, as any visibly transparent plastic having, or capable of being modified to have, as described below, the desired optical properties to render it visibly transparent but capable of absorbing UV radiation, is suitable for use in the present invention.

In order to control the UV absorbance properties of these plastics, one or more UV absorption additives, also known as "UV stabilizers", may be incorporated into the plastic used to produce the spheres during their formation. Although it has been previously known in the art to add UV stabilizers to plastic substrates, such as in the formation of large sheets of UV-absorbent plastic, the incorporation of such UV stabilizers into small plastic spheres of the type described herein has not been previously known for use in sunscreen applications. Such UV additives are well known in the art (see, e.g., Modern Plastic Encyclopedia 1976-1977, pp. 222-227 and 708-709 and U.S. Pat. No. 4,882,143 to Kadokura et al., col. 7 lines 61-65) and include materials such as derivatives of salicylic acid, benzoic acid, cinnamic acid and benzophenone, benzotriazoles, aryl esters, substituted acrylonitrile, metallic complexes and inorganic pigments. The invention should not be limited to the use of these specific materials, however, since any UV additive which serves the intended purpose, i.e., absorbing ultraviolet radiation, can be used with the formulations described with regard to the subject embodiment of the invention.

The inclusion of these additive materials into the plastic spheres described above serves to render these visibly transparent spheres capable of absorbing UV radiation. Thus, upon dispersing these transparent, UV-absorbing spheres in a liquid carrier such as the emulsion described with reference to the embodiment of the invention utilizing substantially pure particles of micronized zinc oxide, in a concentration ranging between about 1-20% by weight of the emulsion and, more preferably, between about 1-10% by weight, the resultant formulation may be topically applied onto the skin of the user, whereupon it remains visibly transparent while absorbing a substantial portion of the UV radiation to which the user is exposed.

Moreover, the particulate sunblock materials described above for inclusion in the topical sunscreen formulations of the present invention may, in still further embodiments of the invention, be incorporated into a variety of cosmetic products such as, for example, lipstick, eyeshadow, foundations, moisturizers, rouge and other personal care products to enhance the ability of these formulations to protect the underlying skin of the user from the damaging effects of UV radiation. These materials may be blended with the cosmetic base by known blending methods such as by means of Henschel mixer, a ribbon mixer, a twin-cylinder mixer or the like.

The amount of such particulate material present within the cosmetic formulations of the invention comprises no more than about 20% by weight, and preferably between about 1-10% by weight. Most preferably, the particulate sunblock agent comprises less than 1% by weight of the total formulation.

The cosmetic formulations described above may also contain a variety of additive materials. These additives are well-known in the art and are added for the purpose of performing their inherent functions. The preferred additives include materials such as thickeners, softeners, superfatting agents, waterproofing agents, emollients, wetting agents and surface-active agents, as well as preservatives, anti-foam agents, perfumes and mixture thereof, or any other compatible ingredient usually employed in cosmetics.

While it is apparent that the invention herein disclosed is well calculated to fulfill the objects above stated, it will be appreciated that numerous modifications and embodiments may be devised by those skilled in the art and it is intended that the appended claims cover all such modifications and embodiments as fall within the true spirit and scope of the present invention.

We claim:

1. A substantially transparent topical sunblock formulation for shielding skin from ultraviolet radiation, said formulation comprising an effective amount of a plurality of particles having a diameter ranging between about 0.01-100 microns formed from a visibly transparent plastic and at least one UV-absorbing compound incorporated into said plastic, said particles dispersed within a substantially colorless dermatologically acceptable liquid carrier in at least an amount sufficient to shield substantially all of said skin over which said formulation is applied from hazardous effects of ultraviolet radiation.

2. The transparent sunblock formulation of claim 1 wherein said visibly transparent plastic is selected from the group consisting of acrylics, styrene polymers, copolymers of styrene and acrylic, styrene acrylonitrile, polycarbonate, methylpentene, terpolymers of acrylonitrile, butadiene and styrene and allyl diglycol carbonate.

3. The transparent sunblock formulation of claim 1 wherein said at least one UV-absorbing compound is selected from the group consisting of benzophenones, cinnamates, salicylates, aminobenzoic acid esters, metallic complexes and inorganic pigments.

4. The transparent sunblock formulation of claim 1 wherein said particles are dispersed within said liquid carrier in the form of an emulsion.

5. The transparent sunblock formulation of claim 1 wherein the concentration of said particles within said liquid carrier is less than about 20% by weight.

6. The transparent sunblock formulation of claim 1 wherein said particles are coated with a coating which reduces optical reflection at an interface between said particles and said liquid carrier.

7. A substantially transparent topical sunblock formulation for shielding skin from ultraviolet radiation, said formulation comprising an effective amount of a plurality of substantially smooth particles having a diameter ranging between about 0.01-100 microns formed from a visibly transparent plastic and at least one UV-absorbing compound incorporated into said plastic, said particles being dispersed within an emulsion of a substantially colorless dermatologically acceptable liquid carrier selected from the group consisting of SD alcohol, lanolin, glyceryl stearate, cocoa butter, sorbitan sesquioleate, propylene glycol, mineral oil, isopropyl myristate, petrolatum, acrylic polymers and mixtures thereof in at least an amount sufficient to shield substantially all of said skin over which said formulation is applied from hazardous effects of ultraviolet radiation.

8. The transparent sunblock formulation of claim 7 wherein said visibly transparent plastic is selected from the group consisting of acrylics, styrene polymers, copolymers of styrene and acrylic, styrene acrylonitrile, polycarbonate, methylpentene, terpolymers of acrylonitrile, butadiene and styrene and allyl diglycol carbonate.

9. The transparent sunblock formulation of claim 7 wherein said at least one UV-absorbing compound is selected from the group consisting of benzophenones, cinnamates, salicylates, aminobenzoic acid esters, metallic complexes and inorganic pigments.

10. The transparent sunblock formulation of claim 7 wherein the concentration of said plastic particles within said liquid carrier is less than about 20% by weight.

11. The transparent sunblock formulation of claim 7 wherein said particles are coated with a coating which reduces optical reflection at an interface between said particles and said liquid carrier.

12. A cosmetic product comprising an effective amount of a plurality of visibly transparent particles having a diameter ranging between about 0.01–100 microns and formed from a visibly transparent plastic having at least one UV-absorbing compound incorporated into said plastic.

13. The cosmetic preparation of claim 12 wherein said visibly transparent plastic is selected from among acrylics, styrene polymers, copolymers of styrene and acrylic, styrene acrylonitrile, polycarbonate, methylpentene, terpolymers of acrylonitrile, butadiene and styrene and allyl diglycol carbonate.

14. The cosmetic product of claim 12 wherein said at least one UV-absorbing compound is selected from the group consisting of benzophenones, cinnamates, salicylates, aminobenzoic acid esters, metallic complexes and inorganic pigments.

* * * * *